US010321711B2

(12) United States Patent
Henry, Jr. et al.

(10) Patent No.: US 10,321,711 B2
(45) Date of Patent: Jun. 18, 2019

(54) PROXIMITY DETECTION FOR AN AEROSOL DELIVERY DEVICE

(71) Applicant: R.J. Reynolds Tobacco Company, Winston-Salem, NC (US)

(72) Inventors: Raymond Charles Henry, Jr., Cary, NC (US); Wilson Christopher Lamb, Hillsborough, NC (US); Glen Joseph Kimsey, Cary, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 991 days.

(21) Appl. No.: 14/609,032

(22) Filed: Jan. 29, 2015

(65) Prior Publication Data

US 2016/0219933 A1 Aug. 4, 2016

(51) Int. Cl.

*A61M 15/06* (2006.01)
*A24F 47/00* (2006.01)
*G08C 17/02* (2006.01)

(52) U.S. Cl.

CPC ............ *A24F 47/008* (2013.01); *G08C 17/02* (2013.01); *G08C 2201/91* (2013.01); *G08C 2201/93* (2013.01)

(58) Field of Classification Search

None
See application file for complete search history.

(56) References Cited

U.S. PATENT DOCUMENTS 1,771,366 A 7/1930 Wyss et al.
2,057,353 A 10/1936 Whittemore, Jr.
2,104,266 A 1/1938 McCormick
3,200,819 A 8/1965 Gilbert
4,284,089 A 8/1981 Ray
(Continued)

FOREIGN PATENT DOCUMENTS

AU 276250 7/1965
CA 2 641 869 5/2010
(Continued)

OTHER PUBLICATIONS

"Bluetooth SIG Finalizes Proximity Profiles for *Bluetooth* Version 4.0," Bluetooth Press Release, 2011, 1 page; http://www.bluetooth.com/Pages/Press-Releases-Detail.aspx?ItemID=134.
(Continued)

*Primary Examiner* — Thor S Campbell
(74) *Attorney, Agent, or Firm* — Womble Bond Dickinson (US) LLP

(57) ABSTRACT

An aerosol delivery device is provided that includes a housing, heating element, communication interface and microprocessor. The heating element may to activate and vaporize components of an aerosol precursor composition in response to a flow of air through at least a portion of the housing, with the air being combinable with a thereby formed vapor to form an aerosol. The communication interface may effect a wireless, proximity-based communication link with a computing device. And the microprocessor may be coupled to the communication interface, may control at least one functional element of the aerosol delivery device based on a state of the proximity-based communication link, or in response to a trigger signal received from the computing device over the proximity-based communication link.

7 Claims, 6 Drawing Sheets

(56) References Cited

U.S. PATENT DOCUMENTS 4,303,083 A 12/1981 Burruss, Jr.
4,735,217 A 4/1988 Gerth et al.
4,848,374 A 7/1989 Chard et al.
4,907,606 A 3/1990 Lilja et al.
4,922,901 A 5/1990 Brooks et al.
4,945,931 A 8/1990 Gori
4,947,874 A 8/1990 Brooks et al.
4,947,875 A 8/1990 Brooks et al.
4,986,286 A 1/1991 Roberts et al.
5,019,122 A 5/1991 Clearman et al.
5,042,510 A 8/1991 Curtiss et al.
5,060,671 A 10/1991 Counts et al.
5,093,894 A 3/1992 Deevi et al.
5,144,962 A 9/1992 Counts et al.
5,249,586 A 10/1993 Morgan et al.
5,261,424 A 11/1993 Sprinkel, Jr.
5,322,075 A 6/1994 Deevi et al.
5,353,813 A 10/1994 Deevi et al.
5,369,723 A 11/1994 Counts et al.
5,372,148 A 12/1994 McCafferty et al.
5,388,574 A 2/1995 Ingebrethsen et al.
5,408,574 A 4/1995 Deevi et al.
5,468,936 A 11/1995 Deevi et al.
5,498,850 A 3/1996 Das
5,505,214 A 4/1996 Collins et al.
5,515,842 A 5/1996 Ramseyer et al.
5,530,225 A 6/1996 Hajaligol
5,564,442 A 10/1996 MacDonald et al.
5,649,554 A 7/1997 Sprinkel et al.
5,666,977 A 9/1997 Higgins et al.
5,687,746 A 11/1997 Rose et al.
5,726,421 A 3/1998 Fleischhauer et al.
5,727,571 A 3/1998 Meiring et al.
5,799,663 A 9/1998 Gross et al.
5,819,756 A 10/1998 Mielordt
5,865,185 A 2/1999 Collins et al.
5,865,186 A 2/1999 Volsey, II
5,878,752 A 3/1999 Adams et al.
5,894,841 A 4/1999 Voges
5,934,289 A 8/1999 Watkins et al.
5,954,979 A 9/1999 Counts et al.
5,967,148 A 10/1999 Harris et al.
6,040,560 A 3/2000 Fleischhauer et al.
6,053,176 A 4/2000 Adams et al.
6,089,857 A 7/2000 Matsuura et al.
6,095,153 A 8/2000 Kessler et al.
6,125,853 A 10/2000 Susa et al.
6,155,268 A 12/2000 Takeuchi
6,164,287 A 12/2000 White
6,196,218 B1 3/2001 Voges
6,196,219 B1 3/2001 Hess et al.
6,598,507 B1 7/2003 Adiga et al.
6,601,776 B1 8/2003 Oljaca et al.
6,615,840 B1 9/2003 Fournier et al.
6,688,313 B2 2/2004 Wrenn et al.
6,772,756 B2 8/2004 Shayan
6,803,545 B2 10/2004 Blake et al.
6,854,461 B2 2/2005 Nichols
6,854,470 B1 2/2005 Pu
7,117,867 B2 10/2006 Cox et al.
7,293,565 B2 11/2007 Griffin et al.
7,513,253 B2 4/2009 Kobayashi et al.
7,775,459 B2 8/2010 Martens, III et al.
7,832,410 B2 11/2010 Hon
7,845,359 B2 12/2010 Montaser
7,896,006 B2 3/2011 Hamano et al.
8,127,772 B2 3/2012 Montaser
8,314,591 B2 11/2012 Terry et al.
8,365,742 B2 2/2013 Hon
8,402,976 B2 3/2013 Fernando et al.
8,499,766 B1 8/2013 Newton
8,528,569 B1 9/2013 Newton
8,550,069 B2 10/2013 Alelov
8,851,081 B2 10/2014 Fernando et al.
8,897,628 B2 * 11/2014 Conley ................. A24F 47/008
392/386
8,910,640 B2 * 12/2014 Sears .................... A24F 47/008
128/202.21
2002/0146242 A1 10/2002 Vieira
2003/0226837 A1 12/2003 Blake et al.
2004/0118401 A1 6/2004 Smith et al.
2004/0129280 A1 7/2004 Woodson et al.
2004/0200488 A1 10/2004 Felter et al.
2004/0226568 A1 11/2004 Takeuchi et al.
2005/0016550 A1 1/2005 Katase
2006/0016453 A1 1/2006 Kim
2006/0196518 A1 9/2006 Hon
2007/0074734 A1 4/2007 Braunshteyn et al.
2007/0102013 A1 5/2007 Adams et al.
2007/0215167 A1 9/2007 Crooks et al.
2007/0267031 A1 11/2007 Hon
2008/0085103 A1 4/2008 Beland et al.
2008/0092912 A1 4/2008 Robinson et al.
2008/0257367 A1 10/2008 Paterno et al.
2008/0276947 A1 11/2008 Martzel
2008/0302374 A1 12/2008 Wengert et al.
2009/0095311 A1 4/2009 Hon
2009/0095312 A1 4/2009 Herbrich et al.
2009/0126745 A1 5/2009 Hon
2009/0188490 A1 7/2009 Hon
2009/0230117 A1 9/2009 Fernando et al.
2009/0272379 A1 11/2009 Thorens et al.
2009/0283103 A1 11/2009 Nielsen et al.
2009/0320863 A1 12/2009 Fernando et al.
2010/0043809 A1 2/2010 Magnon
2010/0083959 A1 4/2010 Siller
2010/0200006 A1 8/2010 Robinson et al.
2010/0229881 A1 9/2010 Hearn
2010/0242974 A1 9/2010 Pan
2010/0307518 A1 12/2010 Wang
2010/0313901 A1 12/2010 Fernando et al.
2011/0005535 A1 1/2011 Xiu
2011/0011396 A1 1/2011 Fang
2011/0036363 A1 2/2011 Urtsev et al.
2011/0036365 A1 2/2011 Chong et al.
2011/0094523 A1 4/2011 Thorens et al.
2011/0126848 A1 6/2011 Zuber et al.
2011/0155153 A1 6/2011 Thorens et al.
2011/0155718 A1 6/2011 Greim et al.
2011/0168194 A1 7/2011 Hon
2011/0265806 A1 11/2011 Alarcon et al.
2011/0309157 A1 12/2011 Yang et al.
2012/0042885 A1 2/2012 Stone et al.
2012/0060853 A1 3/2012 Robinson et al.
2012/0111347 A1 5/2012 Hon
2012/0132643 A1 5/2012 Choi et al.
2012/0227752 A1 9/2012 Alelov
2012/0231464 A1 9/2012 Yu et al.
2012/0260927 A1 10/2012 Liu
2012/0279512 A1 11/2012 Hon
2012/0318882 A1 12/2012 Abehasera
2013/0037041 A1 2/2013 Worm et al.
2013/0056013 A1 3/2013 Terry et al.
2013/0081625 A1 4/2013 Rustad et al.
2013/0081642 A1 4/2013 Safari
2013/0192619 A1 8/2013 Tucker et al.
2013/0206154 A1 8/2013 Fernando et al.
2013/0284192 A1 10/2013 Peleg et al.
2013/0306084 A1 11/2013 Flick
2013/0319439 A1 12/2013 Gorelick et al.
2013/0340750 A1 12/2013 Thorens et al.
2013/0340775 A1 12/2013 Juster et al.
2014/0014125 A1 * 1/2014 Fernando ............. A24F 47/008
131/328
2014/0060554 A1 3/2014 Collett et al.
2014/0060555 A1 3/2014 Chang et al.
2014/0096781 A1 4/2014 Sears et al.
2014/0096782 A1 4/2014 Ampolini et al.
2014/0174459 A1 6/2014 Burstyn
2014/0209105 A1 * 7/2014 Sears .................... A24F 47/008
131/328
2014/0246035 A1 9/2014 Minskoff et al.
2015/0007838 A1 1/2015 Fernando et al.

(56) References Cited

U.S. PATENT DOCUMENTS

| | | | | |
|---|---|---|---|---|
| 2015/0020833 A1* | 1/2015 | Conley | A24F 47/008 131/329 |
| 2015/0068541 A1* | 3/2015 | Sears | A24F 47/008 131/328 |
| 2015/0223522 A1* | 8/2015 | Ampolini | A24F 47/008 131/328 |
| 2015/0238713 A1* | 8/2015 | Cohen | A61M 15/0065 128/200.14 |
| 2015/0245662 A1* | 9/2015 | Memari | A24F 15/12 131/328 |
| 2015/0245663 A1* | 9/2015 | Memari | A24F 15/12 131/329 |
| 2015/0245664 A1* | 9/2015 | Memari | A24F 15/12 131/329 |
| 2015/0245665 A1* | 9/2015 | Memari | A24F 15/12 131/329 |
| 2015/0245666 A1* | 9/2015 | Memari | A24F 15/12 131/329 |
| 2015/0245667 A1* | 9/2015 | Memari | A24F 15/12 131/329 |
| 2015/0359266 A1* | 12/2015 | Memari | A24F 15/12 131/328 |
| 2016/0050975 A1* | 2/2016 | Worm | A24F 47/008 131/328 |
| 2016/0150824 A1* | 6/2016 | Memari | A24F 15/12 131/329 |
| 2016/0198771 A1* | 7/2016 | Goggin | A24F 47/008 131/329 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| GB | 2516131 A | 1/2015 |
| WO | WO 1997/48293 | 12/1997 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |

OTHER PUBLICATIONS

"Electronic leash" (definition), *Wikipedia, the free encyclopedia*, 1 page; http://en.wikipedia.org/w/index.php?title=Electronic_leash&printable=yes.

"Nordic Semiconductor ASA is predicting that mass-market wireless proximity and security sensing will be viable for the first time following Bluetooth SIG's recent finalization of its Bluetooth low energy Find Me and Proximity profiles—part of the latest Bluetooth Version 4.0 (v4.0) specification," *EE Times Europe*, 2015, 1 page; http://www.analog-eetimes.com/_includes/print.php?1g=en&cmp_id=17&safe_mode=.

"ProximoTM—Find your Phone & Items Easily," Kensington, 2015, pp. 1-11; http://www.kensington.com/us/us/4570/proximo-find-your-phone-items-easily.

"StickNFind system uses your phone and coin-like tags to find lost items," *Highlights from CES*, 2012, pp. 1-13; http://gizmag.com/sticknfind-finding-system/25238/.

International Search Report and Written Opinion dated Apr. 21, 2016 for Application No. PCT/US2016/015313.

* cited by examiner

PROXIMITY DETECTION FOR AN AEROSOL DELIVERY DEVICE

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., all of which are incorporated herein by reference in their entireties. See also, for example, the various types of smoking articles, aerosol delivery devices and electrically-powered heat generating sources referenced by brand name and commercial source in U.S. patent application Ser. No. 14/170,838 to Bless et al., filed Feb. 3, 2014, which is incorporated herein by reference in its entirety. Additionally, other types of smoking articles have been proposed in U.S. Pat. No. 5,505,214 to Collins et al., U.S. Pat. No. 5,894,841 to Voges, U.S. Pat. No. 6,772,756 to Shayan, U.S. Pat. App. Pub. No. 2006/0196518 to Hon, and U.S. Pat. App. Pub. No. 2007/0267031 to Hon, all of which are incorporated herein by reference in their entireties.

It would be desirable to provide a smoking article that employs heat produced by electrical energy to provide the sensations of cigarette, cigar, or pipe smoking, that does so without combusting or pyrolyzing tobacco to any significant degree, that does so without the need of a combustion heat source, and that does so without necessarily delivering considerable quantities of incomplete combustion and pyrolysis products. Further, advances with respect to manufacturing electronic smoking articles would be desirable.

BRIEF SUMMARY

The present disclosure relates to aerosol delivery devices, methods of forming such devices, and elements of such devices. According to one aspect of example implementations of the present disclosure, an aerosol delivery device is provided. The aerosol delivery device includes a housing, heating element, communication interface and microprocessor. The heating element may be configured to activate and vaporize components of an aerosol precursor composition in response to a flow of air through at least a portion of the housing, with the air being combinable with a thereby formed vapor to form an aerosol. The communication interface may be configured to effect a wireless, proximity-based communication link with a computing device. And the microprocessor may be coupled to the communication interface and configured to control at least one functional element of the aerosol delivery device based on a state of the proximity-based communication link, or in response to a trigger signal received from the computing device over the proximity-based communication link.

In some examples, the microprocessor may be configured to control the functional element(s) of the aerosol delivery device in an instance in which the proximity-based communication link is broken.

In some examples, the microprocessor may be configured to control the functional element(s) of the aerosol delivery device based on a signal strength of the proximity-based communication link.

In some examples, the microprocessor being configured to control at least one functional element of the aerosol delivery device may include being configured to control a sensory-feedback member to provide a user-perceptible feedback.

In some examples, the microprocessor being configured to control at least one functional element of the aerosol delivery device may include being configured to control at least one functional element to alter a locked state of the aerosol delivery device.

According to another aspect of example implementations of the present disclosure, a computing device is provided. The computing device includes a communication interface and processor. The communication interface may be configured to effect a wireless, proximity-based communication link with an aerosol delivery device including a housing and heating element. Similar to before, the heating element may be configured to activate and vaporize components of an aerosol precursor composition in response to a flow of air through at least a portion of the housing, with the air being combinable with a thereby formed vapor to form an aerosol.

The processor of the computing device may be coupled to the communication interface and configured to control at least one functional element of the computing device based on a state of the proximity-based communication link. Or the processor may be configured to cause transmission of a trigger signal to the aerosol delivery device over the proximity-based communication link to effect control of the aerosol delivery device in response thereto.

In some examples, the processor may be configured to control the functional element(s) of the computing device, and in an instance in which the proximity-based communication link is broken.

In some examples, the processor may be configured to control the functional element(s) of the computing device, and based on a signal strength of the proximity-based communication link.

In some examples, the processor may be configured to cause transmission of the trigger signal, including being configured to cause transmission of the trigger signal to effect control of a sensory-feedback member of the aerosol delivery device to provide a user-perceptible feedback.

In some examples, the processor may be configured to cause transmission of the trigger signal, including being configured to cause transmission of the trigger signal to alter a locked state of the aerosol delivery device.

In other aspects of example implementations, methods are provided for respectively controlling operation of and interacting with an aerosol delivery device. The features, functions and advantages discussed herein may be achieved independently in various example implementations or may be combined in yet other example implementations further details of which may be seen with reference to the following description and drawings.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

Figure 1:
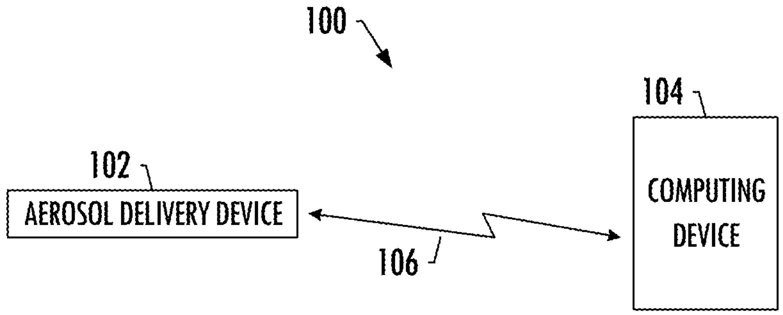
FIGS. 1 and 2 illustrate respective systems according to example implementations of the present disclosure, each of which includes an aerosol delivery device and computing device.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems, and control or interaction with such aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and removably attached thereto an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

Figure 2:
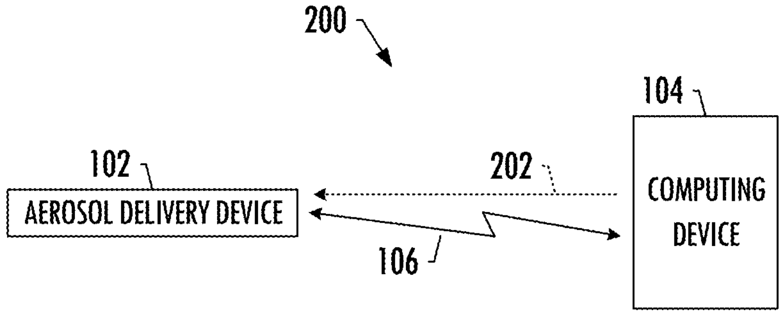

FIGS. 1 and 2 illustrate respective systems 100, 200 according to example implementations of the present disclosure, each of which includes an aerosol delivery device 102 and computing device 104. As shown and described in greater detail below, the system 100 shown in FIG. 1 may be a system for controlling operation of an aerosol delivery device. And the system 200 shown in FIG. 2 may be a system for interacting with an aerosol delivery device. The aerosol delivery device and computing device may be the same in either system. In some examples, however, the aerosol delivery device may differ between the systems, at least in its functionality. Similarly, in some examples, the computing device may differ between the systems, at least in its functionality.

The aerosol delivery device 102 may be embodied as any of a number of different devices that include at least a heating element configured to activate and vaporize components of an aerosol precursor composition in response to a flow of air through at least a portion of the housing, with the air being combinable with a thereby formed vapor to form an aerosol. The computing device 104 may also be embodied as a number of different devices, such as any of a number of different mobile computers. More particular examples of suitable mobile computers include portable computers (e.g., laptops, notebooks, tablet computers), mobile phones (e.g., cell phones, smartphones), wearable computers (e.g., smartwatches) and the like. In other examples, the computing device may be embodied as other than a mobile computer, such as in the manner of a desktop computer, server computer or the like. And in yet another example, the computing device may be embodied as an electric beacon such as one employing iBeacon™ technology developed by Apple Inc.

As shown, the aerosol delivery device 102 and computing device 104 may be paired to establish a proximity-based communication link 106 between the devices to allow wireless communication between them. This proximity-based communications link may be supported by one or more of a number of different proximity-based, device-to-device communication technologies. Examples of suitable technologies include various near field communication (NFC) technologies, wireless personal area network (WPAN) technologies and the like. More particular examples of suitable WPAN technologies include those specified by IEEE 802.15 standards or otherwise, including Bluetooth, Bluetooth low energy (Bluetooth LE), ZigBee, infrared (e.g., IrDA), radio-frequency identification (RFID), Wireless USB and the like. Yet other examples of suitable proximity-based, device-to-device communication technologies include Wi-Fi Direct, as well as certain other technologies based on or specified by IEEE 802.11 standards and that support direct device-to-device communication.

In accordance with example implementations of the present disclosure, the system 100, 200 may provide a number of proximity-based services based on or carried over the proximity-based communication link 106. In some examples, the aerosol delivery device 102 and/or computing device 104 may be configured to perform one or more operations based on a state of the proximity-based communication link. The state of the proximity-based communication link may be indicated in a number of different manners, such as by its existence whereby the device(s) may perform one or more operations in an instance in which the proximity-based communication link is established or broken. In another example, the state of the proximity-based communication link may be indicated by its signal strength, which in some examples may be given by a received signal strength indicator (RSSI) (i.e., power present in a received signal over the communication link).

The operation(s) performed by the aerosol delivery device 102 and/or computing device 104 based on the state of the proximity-based communication link 106 may include the device(s) being configured provide a user-perceptible feedback. This feedback may include a visual, audible and/or haptic (e.g., vibration) feedback. Additionally or alternatively, the operation(s) may include the aerosol delivery device being configured to alter a locked state of the aerosol delivery device. Thus, for example, the device(s) may provide a user-perceptible feedback in an instance in which the proximity-based communication link is broken or its signal strength reduces to below a threshold level (indicating an increased distance between the aerosol delivery device and computing device). Additionally or alternatively, for example, the aerosol delivery device may be locked whereby the device or more specifically one or more of its components (e.g., heating element) may be disabled.

As shown more particularly in the system 200 of FIG. 2, in some examples, the computing device 104 may be configured to transmit a trigger signal 202 to the aerosol delivery device 102 over the proximity-based communication link 106 to effect control of the aerosol delivery device in response thereto. In some examples, transmission of the trigger signal may be initiated by a user of the computing device, such as by specific user-selection or a schedule specified or selected by the user. In other examples, transmission of the trigger signal may be initiated in when one or more conditions are satisfied, which may or may not be user-specified.

The aerosol delivery device 102 may be configured to perform one or more operations in response to the trigger signal received from the computing device 104 over the proximity-based communication link 106. The operation(s) performed by the aerosol delivery device may include it being configured provide a user-perceptible feedback (e.g., visual, audible and/or haptic feedback). Additionally or alternatively, the operation(s) may include the aerosol delivery device being configured to alter a locked state of the aerosol delivery device. Thus, for example, the aerosol delivery device may provide a user-perceptible feedback in response to the trigger signal, which may allow the user to locate their aerosol delivery device. Additionally or alternatively, for example, the aerosol delivery device may be locked in response to the trigger signal, which may allow the user to remotely lock their aerosol delivery device.

In some other examples, a computing device 104 embodied as an electric beacon may transmit a trigger signal to control the aerosol delivery device 102 when it detects and pairs with the aerosol delivery device to establish the proximity-based communication link. The trigger signal may cause the aerosol delivery device to lock or unlock, which may allow one to prevent or allow usage of the aerosol delivery device in the environment where the electric beacon is located. In another example, the trigger signal may cause the aerosol delivery device to operate with certain variable parameters such as a higher output power (increased vapor), different flavor triggers or the like.

Figure 3:
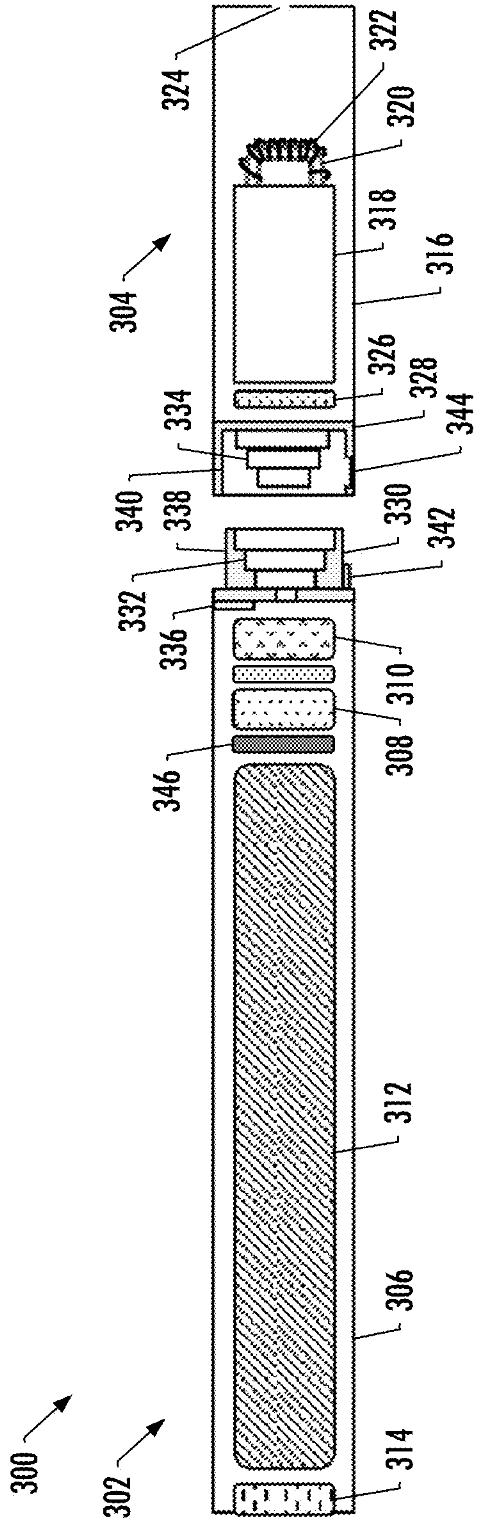
FIG. 3 is a partially cut-away view of an aerosol delivery device that in some examples may correspond to the aerosol delivery device of FIG. 1, according to various example implementations of the present disclosure.
Figure 4:
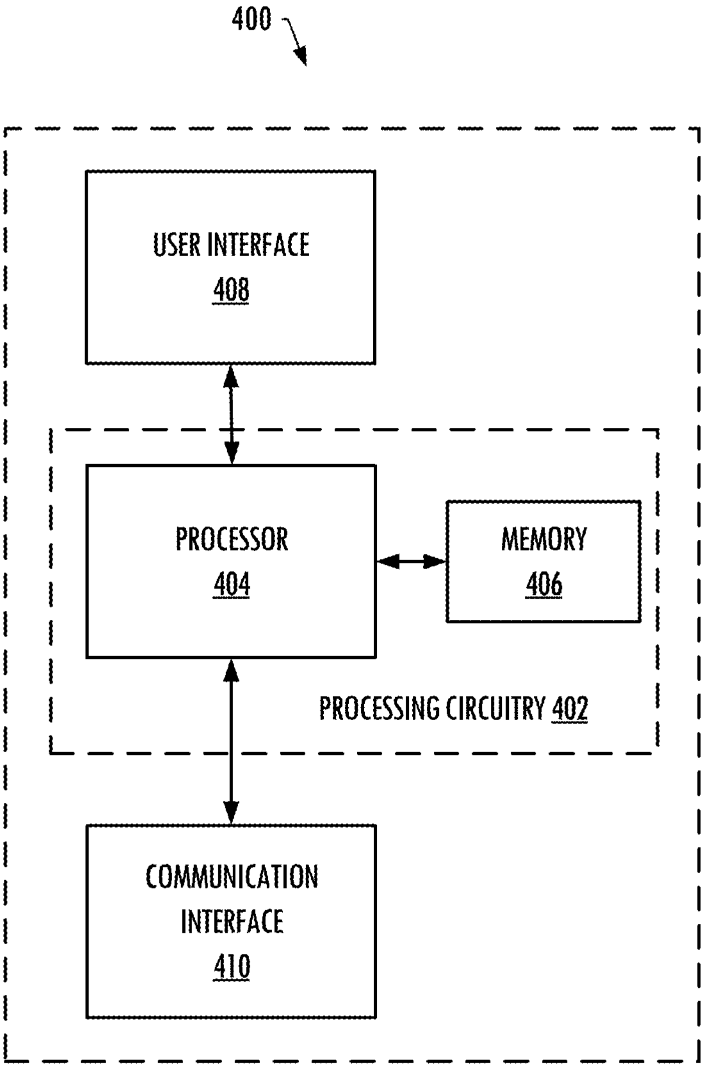
FIG. 4 illustrates a computing device that in some examples may correspond to the computing device of FIG. 1, according to various example implementations of the present disclosure.

Reference will now be made to FIGS. 3 and 4, which illustrate more particular examples of a suitable aerosol delivery device and computing device, respectively, according to example implementations of the present disclosure.

FIG. 3 illustrates an aerosol delivery device 300 that in some examples may correspond to the aerosol delivery device 102 of FIGS. 1 and 2. As seen in the cut-away view illustrated therein, the aerosol delivery device can comprise a control body 302 and a cartridge 304 that can be permanently or detachably aligned in a functioning relationship. Engagement of the control body and the cartridge can be press fit (as illustrated), threaded, interference fit, magnetic or the like. In particular, connection components, such as further described herein may be used. For example, the control body may include a coupler that is adapted to engage a connector on the cartridge.

In specific example implementations, one or both of the control body 302 and the cartridge 304 may be referred to as being disposable or as being reusable. For example, the control body may have a replaceable battery or a rechargeable battery and thus may be combined with any type of recharging technology, including connection to a typical electrical outlet, connection to a car charger (i.e., cigarette lighter receptacle), and connection to a computer, such as through a universal serial bus (USB) cable. For example, an adaptor including a USB connector at one end and a control body connector at an opposing end is disclosed in U.S. Pat. App. Pub. No. 2014/0261495 to Novak et al., which is incorporated herein by reference in its entirety. Further, in some examples the cartridge may comprise a single-use cartridge, as disclosed in U.S. Pat. App. Pub. No. 2014/0060555 to Chang et al., which is incorporated herein by reference in its entirety.

As illustrated in FIG. 3, the control body 302 can be formed of a control body shell 306 that can include a control component 308 (e.g., a microprocessor, individually or as part of a microcontroller), a flow sensor 310, a battery 312 and a light-emitting diode (LED) 314, and such components can be variably aligned. Further indicators (e.g., a haptic feedback component, an audio feedback component, or the like) can be included in addition to or as an alternative to the LED. The cartridge 304 can be formed of a cartridge shell 316 enclosing a reservoir 318 that is in fluid communication with a liquid transport element 320 adapted to wick or otherwise transport an aerosol precursor composition stored in the reservoir housing to a heater 322 (sometimes referred to as a heating element). In some example, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 322. The heater in these examples may be resistive heating element such as a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 3 as described herein.

An opening 324 may be present in the cartridge shell 316 (e.g., at the mouthend) to allow for egress of formed aerosol from the cartridge 304. Such components are representative of the components that may be present in a cartridge and are not intended to limit the scope of cartridge components that are encompassed by the present disclosure.

The cartridge 304 also may include one or more electronic components 326, which may include an integrated circuit, a memory component, a sensor, or the like. The electronic components may be adapted to communicate with the control component 308 and/or with an external device by wired or wireless means. The electronic components may be positioned anywhere within the cartridge or a base 328 thereof.

Although the control component 308 and the flow sensor 310 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 302 and the cartridge 304 may include components adapted to facilitate a fluid engagement therebetween. As illustrated in FIG. 3, the control body can include a coupler 330 having a cavity 332 therein. The base 328 of the cartridge can be adapted to engage the coupler and can include a projection 334 adapted to fit within the cavity. Such engagement can facilitate a stable connection between the control body and the cartridge as well as establish an electrical connection between the battery 312 and control component 308 in the control body and the heater 322 in the cartridge. Further, the control body shell 306 can include an air intake 336, which may be a notch in the shell where it connects to the coupler that allows for passage of ambient air around the coupler and into the shell where it then passes through the cavity 332 of the coupler and into the cartridge through the projection 334.

A coupler and a base useful according to the present disclosure are described in U.S. Pat. App. Pub. No. 2014/0261495 to Novak et al., which is incorporated herein by reference in its entirety. For example, the coupler 330 as seen in FIG. 3 may define an outer periphery 338 configured to mate with an inner periphery 340 of the base 328. In one example the inner periphery of the base may define a radius that is substantially equal to, or slightly greater than, a radius of the outer periphery of the coupler. Further, the coupler may define one or more protrusions 342 at the outer periphery configured to engage one or more recesses 344 defined at the inner periphery of the base. However, various other examples of structures, shapes and components may be employed to couple the base to the coupler. In some examples the connection between the base of the cartridge 304 and the coupler of the control body 302 may be substantially permanent, whereas in other examples the connection therebetween may be releasable such that, for example, the control body may be reused with one or more additional cartridges that may be disposable and/or refillable.

The aerosol delivery device 300 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 318 illustrated in FIG. 3 can be a container or can be a fibrous reservoir, as presently described. For example, the reservoir can comprise one or more layers of nonwoven fibers substantially formed into the shape of a tube encircling the interior of the cartridge shell 316, in this example. An aerosol precursor composition can be retained in the reservoir. Liquid components, for example, can be sorptively retained by the reservoir. The reservoir can be in fluid connection with the liquid transport element 320. The liquid transport element can transport the aerosol precursor composition stored in the reservoir via capillary action to the heater 322 that is in the foam of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 3 as described herein. In particular, specific combinations of heating members and transport elements as further described below may be incorporated into devices such as illustrated in FIG. 3 as described herein.

In use, when a user draws on the aerosol delivery device 300, airflow is detected by the flow sensor 310, and the heater 322 is activated to vaporize components of the aerosol precursor composition. Drawing upon the mouthend of the aerosol delivery device causes ambient air to enter the air intake 336 and pass through the cavity 332 in the coupler 330 and the central opening in the projection 334 of the base 328. In the cartridge 304, the drawn air combines with the formed vapor to form an aerosol. The aerosol is whisked, aspirated or otherwise drawn away from the heater and out the opening 324 in the mouthend of the aerosol delivery device.

In some examples, the aerosol delivery device 300 may include a number of additional software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 308 may be configured to control at least one functional element to inhibit battery charging if the ambient temperature is below a certain temperature (e.g., 0° C.) or above a certain temperature (e.g., 45° C.) prior to start of charging or during charging.

Power delivery from the battery 312 may vary over the course of each puff on the device 300 according to a power control mechanism. The device may include a "long puff" safety timer such that in the event that a user or an inadvertent mechanism causes the device to attempt to puff continuously, the control component 308 may control at least one functional element to terminate the puff automatically after some period of time (e.g., four seconds). Further, the time between puffs on the device may be restricted to less than a period of time (e.g., 100). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 310, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 300 may include a puff tracking algorithm configured for heater lockout once a defined number of puffs has been achieved for an attached cartridge (based on the number of available puffs calculated in light of the e-liquid charge in the cartridge). The aerosol delivery device may include a sleep, standby or low-power mode function whereby power delivery may be automatically cut off after a defined period of non-use. Further safety protection may be provided in that all charge/discharge cycles of the battery 312 may be monitored by the control component 308 over its lifetime. After the battery has attained the equivalent of a predetermined number (e.g., 200) full discharge and full recharge cycles, it may be declared depleted, and the control component may control at least one functional element to prevent further charging of the battery.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 300 can incorporate the sensor 310 or another sensor or detector for control of supply of electric power to the heater 322 when aerosol generation is desired (e.g., upon draw during use). As such, for example, there is provided a manner or method of turning off the power supply to the heater when the aerosol delivery device is not be drawn upon during use, and for turning on the power supply to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 300 most preferably incorporates the control component 308 or another control mechanism for controlling the amount of electric power to the heater 322 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and *Chemical and Biological Studies on New Cigarette Prototypes that Heat Instead of Burn Tobacco*, R. J. Reynolds Tobacco Company Monograph (1988), all of which are incorporated herein by reference in their entireties.

Additional representative types of components that yield visual cues or indicators may be employed in the aerosol delivery device 300, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

In accordance with example implementations of the present disclosure, the aerosol delivery device 300 may further include a communication interface 346 configured to effect a wireless, proximity-based communication link (e.g., proximity-based communication link 106) with a computing device (e.g., computing device 104). The control component 308 (e.g., microprocessor) may be coupled to the communication interface and configured to control at least one functional element of the aerosol delivery device based on a state of the proximity-based communication link, or in response to a trigger signal received from the computing device over the proximity-based communication link.

In some examples, the control component 308 may be configured to control the functional element(s) of the aerosol delivery device 300 in an instance in which the proximity-based communication link is broken. Additionally or alternatively, in some examples, the control component may be configured to control the functional element(s) of the aerosol delivery device based on a signal strength (e.g., RSSI) of the proximity-based communication link.

Functional element(s) of the aerosol delivery device 300 may be controlled in any of a number of different manners based on the state of the proximity-based communication link, or in response to a trigger signal received over the link. For example, the control component 308 may be configured to control a sensory-feedback member (e.g., a LED, auditory element, vibratory element) to provide a user-perceptible feedback (e.g., visual, audible, haptic feedback). Additionally or alternatively, for example, the control component may be configured to control at least one functional element to alter a locked state of the aerosol delivery device. This may include, for example, disabling one or more components of the aerosol delivery device, such as the heater 322.

FIG. 4 illustrates a computing device 400 that in some examples may correspond to the computing device 104 of FIGS. 1 and 2. It will be appreciated that the components, devices or elements illustrated in and described with respect to FIG. 4 below may not be mandatory and thus some may be omitted in certain examples. Additionally, some examples may include further or different components, devices or elements beyond those illustrated in and described with respect to FIG. 4.

As shown, the computing device 400 may include processing circuitry 402 configurable to perform functions in accordance with one or more example implementations described herein. More particularly, for example, the processing circuitry may be configured to perform data processing, application execution and/or other processing and management services according to one or more example implementations.

In some examples, the computing device 400 or a portion(s) or component(s) thereof, such as the processing circuitry 402, may be implemented via one or more integrated circuits, which may each include one or more chips. The processing circuitry and/or one or more further components of the computing device may therefore, in some instances, be implemented as a system on a chip.

In some examples, the processing circuitry 402 may include a processor 404 and, in some examples, such as that illustrated in FIG. 4, may further include memory 406. The processing circuitry may be in communication with or otherwise control one or more of each of a number of components such as a user interface 408, communication interface 410 and the like.

The processor 404 may be embodied in a variety of forms. For example, the processor may be embodied as various hardware processing means, such as a microprocessor, a coprocessor, a controller or various other computing or processing devices including integrated circuits such as, for example, an ASIC (application specific integrated circuit), an FPGA (field programmable gate array), some combination thereof, or the like. Although illustrated as a single processor, it will be appreciated that the processor may comprise a plurality of processors. The plurality of processors may be in operative communication with each other and may be collectively configured to perform one or more functions described herein. In some examples, the processor may be configured to execute instructions that may be stored in the memory 406 and/or that may be otherwise accessible to the processor. As such, whether configured by hardware or by a combination of hardware and software, the processor may be capable of performing operations according to various examples while being configured accordingly.

In some examples, the memory 406 may include one or more memory devices. The memory may include fixed and/or removable memory devices. In some examples, the memory may provide a non-transitory computer-readable storage medium that may store computer program instructions that may be executed by the processor 404. In this regard, the memory may be configured to store information, data, applications, instructions and/or the like for enabling the computing device 400 to carry out various functions in accordance with one or more example implementations of the present disclosure. In some examples, the memory may be in communication with one or more of the processor, user interface 408 or communication interface 410 via one or more buses for passing information among components of the computing device.

In some examples, the computing device 400 may include one or more user interfaces 408. The user interface may be in communication with the processing circuitry 402 to receive an indication of a user input and/or to provide an audible, visual, tactile, mechanical or other output to a user. As such, the user interface may include, for example, a keyboard, a mouse, a joystick, a display, a touch screen display, a microphone, a speaker, a vibration motor, one or more biometric input devices (e.g., a visual or sensorial tracing device that may track body part or eye movements), an accelerometer, a gyroscope, and/or other input/output mechanisms. In examples in which the user interface includes a touch screen display, the user interface may additionally be configured to detect and/or receive an indication of a touch and/or other movement gesture or other input to the display. The user interface may, for example, be configured to display a graphical user interface (GUI) of a software application running on the computing device, and through which an aerosol delivery device (e.g., aerosol delivery device 102) may be controlled, or interaction with an aerosol delivery device may be carried out. The user interface may further provide an input mechanism(s) for enabling the user to select the command, which may accordingly be received by the apparatus via the user interface.

The computing device 400 may further include one or more communication interfaces 410, which may enable the computing device to communicate with one or more networks, other computing devices, or other appropriately-enabled devices such as an aerosol delivery device (e.g., aerosol delivery device 102). The communication interface may include, for example, an antenna (or multiple antennas) and supporting hardware and/or software for enabling communications with a wireless communication network (e.g., a cellular network, Wi-Fi, WLAN, and/or the like) and/or for supporting a wireless communication link (e.g., proximity-based communication link 106). For example, the communication interface may be configured to support various wireless, proximity-based device-to-device communication technologies, such as those described above. In some examples, the communication interface may include a communication modem, a physical port (e.g., a serial port) for receiving a wired communication cable, and/or other hardware/software for supporting communication via cable, digital subscriber line (DSL), USB, FireWire, Thunderbolt, Ethernet, one or more optical transmission technologies, and/or other wired communication technology that may be used to implement a wired communication link.

In accordance with example implementations of the present disclosure, the communication interface 410 may be configured to effect a wireless, proximity-based communication link (e.g., proximity-based communication link 106) with an aerosol delivery device (e.g., aerosol delivery device 102). The processor 404 may be coupled to the communication interface and configured to control at least one functional element of the computing device 400 based on a state of the proximity-based communication link, or cause transmission of a trigger signal to the aerosol delivery device over the proximity-based communication link to effect control of the aerosol delivery device in response thereto.

In some examples, the processor 404 may be configured to control the functional element(s) of the computing device 400 in an instance in which the proximity-based communication link is broken. Additionally or alternatively, in some examples, the processor may be configured to control the functional element(s) of the computing device based on a signal strength (e.g., RSSI) of the proximity-based communication link. In any instance, however, functional element(s) of the computing device may be controlled in any of a number of different manners based on the state of the proximity-based communication link. For example, the processor may be configured to control one or more user interfaces (e.g., display, speaker, vibration motor) to provide a user-perceptible feedback (e.g., visual, audible, haptic feedback).

In some examples, the processor 404 may be configured to cause transmission of the trigger signal to effect control of the aerosol delivery device, in any of a number of different manners. In response to the trigger signal, for example, a sensory-feedback member (e.g., a LED, auditory element, vibratory element) of the aerosol delivery device may be controlled to provide a user-perceptible feedback (e.g., visual, audible, haptic feedback). Additionally or alternatively, for example, a locked state of the aerosol delivery device may be altered in response to the trigger signal. This may include, for example, disabling one or more components of the aerosol delivery device, such as a heating element of the aerosol delivery device.

Briefly returning to FIG. 1, in some examples, the computing device 104 may execute a software application (that may run on the computing device). This software application may provide a GUI through which control of or interaction with the aerosol delivery device 102 may be carried out, in accordance with various example implementations. The GUI may provide access to one or more selectable commands for controlling or interacting with the aerosol delivery device, and/or device status or other information regarding the aerosol delivery device. A user may select a command, such as by touching an appropriate region of a touch screen display, providing a voice command, and/or actuating an appropriate key, button, or other input mechanism that may be provided by a user interface of the computing device. The computing device may receive an indication of a command selected by the user, and may determine one or more operations corresponding to the command. The computing device may format and send one or more messages, including a trigger signal in some examples, to invoke performance of one or more commanded operations by the aerosol delivery device in response to the user command. In some examples, this may be accomplished through messages embodied as read requests, such as in the manner described by U.S. patent application Ser. No. 14/327,776 to Ampolini et al., filed Jul. 10, 2014, which is incorporated herein by reference in its entirety.

To further illustrate aspects of example implementations of the present disclosure, reference is now made to FIGS. 5-8, which illustrate an example GUI of a suitable software application for control of or interaction with an aerosol delivery device.

Figure 5:
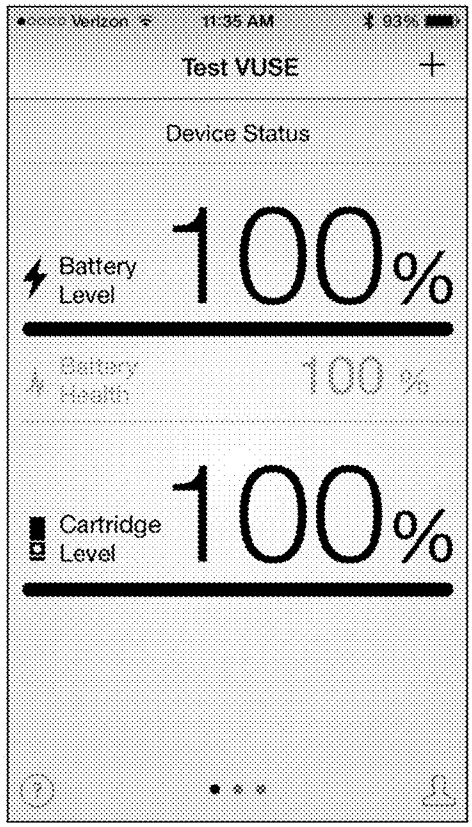
FIGS. 5-8 illustrate an example graphical user interface (GUI) of a suitable software application for control of or interaction with an aerosol delivery device, according to example implementations.

As shown in FIG. 5, the GUI may display device status information regarding the aerosol delivery device 102, which may be reported to the computing device 104 on-demand or with some frequency. This information may include a battery level, battery health and/or cartridge level. The battery level may indicate a current percentage charge of the battery (e.g., battery 312) of the aerosol delivery device. The battery health may indicate a current health of the battery relative to a new battery. In some examples, the battery health may indicate a number of charge/discharge cycles of the battery that may remain in a predetermined number (e.g., 200) designated to constitute its lifetime. And the cartridge level may indicate an amount of aerosol precursor composition remaining in a cartridge of the aerosol delivery device (e.g., cartridge 304).

Figure 6:
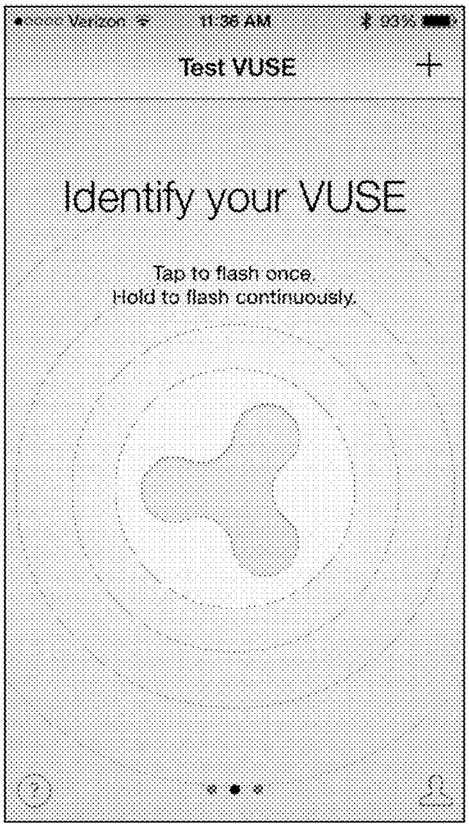

As shown in FIG. 6, the GUI may enable the user to validate their aerosol delivery device 102 to the software application running on the computing device 104. In some examples, this may include user input to cause the software application and in turn the computing device to transmit a trigger signal 202 to the aerosol delivery device over the proximity-based communication link. In response, the aerosol delivery device may provide a user-perceptible feedback such as a single or continuous LED flash depending on the user input.

Figure 7:
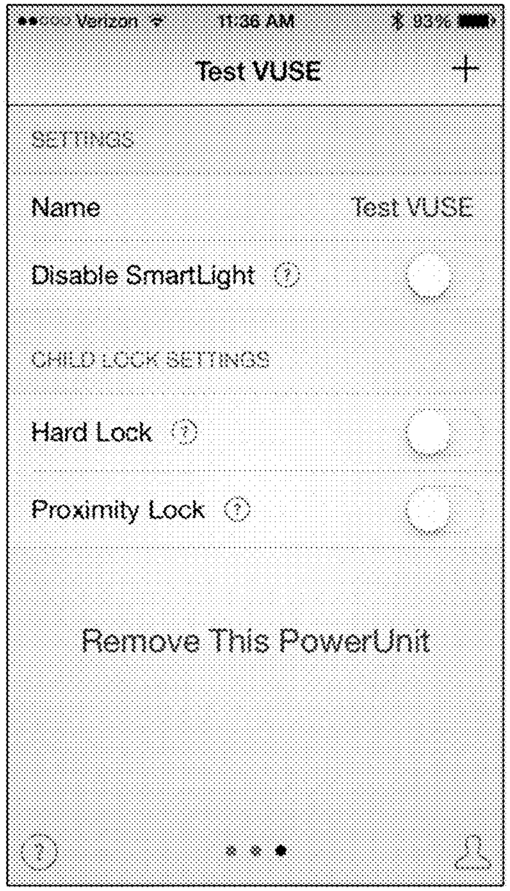

FIG. 7 illustrates an example in which the GUI may provide access to one or more selectable commands for controlling or interacting with the aerosol delivery device 102. Through these commands, a user may disable a sensory-feedback member (e.g., LED 314). Additionally or alternatively, for example, a use may initiate a hard lock or a proximity lock of the aerosol delivery device. Selection of the hard lock command may cause the software application and in turn the computing device to transmit a trigger signal 202 to the aerosol delivery device over the proximity-based communication link, in response to which the aerosol delivery device may be locked. Selection of the proximity lock command may cause a similar transmission of a trigger signal. In this instance, however, the signal may enable the aerosol delivery device to lock an instance in which the proximity-based communication link 106 is broken or its signal strength reduces to below a threshold level (indicating an increased distance between the aerosol delivery device and computing device 106). In some examples, repairing of the aerosol delivery device and computing device to reestablish the proximity-based communication link may be required to unlock the aerosol delivery device. And as also shown, the commands may enable the user to terminate the proximity-based communication link between the devices.

Figure 8:
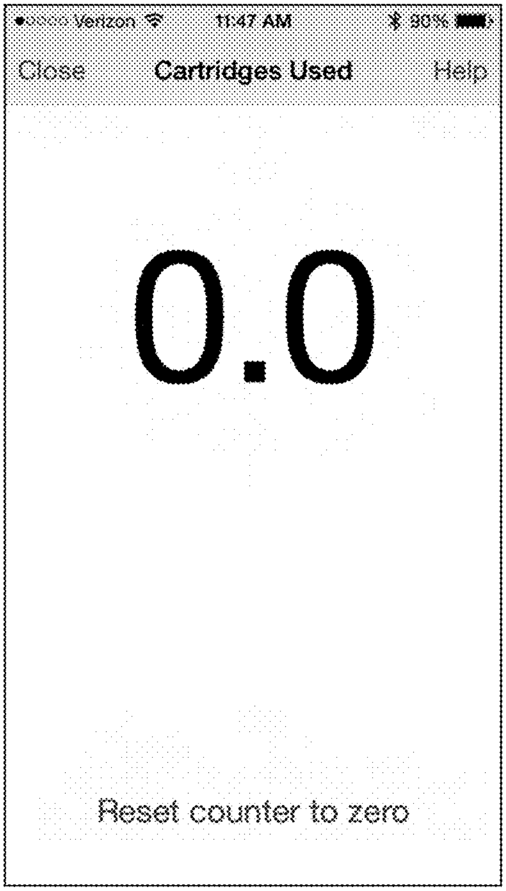

FIG. 8 illustrates additional information that may be provided by the GUI, according to some example implementations. As shown, the GUI may maintain a counter of a number of cartridges that have been used with the aerosol delivery device 102. In some examples, this may be managed by the user. In other examples, it may be automatically managed based on indications from the aerosol delivery device that its cartridge has been replaced. And in some examples, the counter may be reset by the user on-demand, regardless of how the counter is managed.

Figure 9:
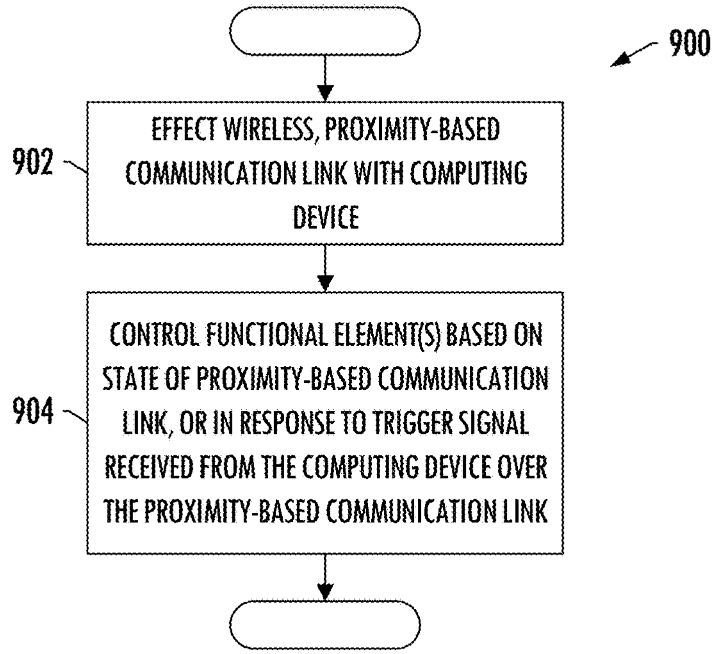
FIG. 9 illustrates various operations in a method of controlling operation of an aerosol delivery device, according to example implementations.

FIG. 9 illustrates various operations in a method 900 of controlling operation of an aerosol delivery device including a heating element configured to activate and vaporize components of an aerosol precursor composition in response to a flow of air through at least a portion of the housing, with the air being combinable with a thereby formed vapor to form an aerosol. The method includes operations performed at the aerosol delivery device. As shown at block 902, these operations may include effecting a wireless, proximity-based communication link with a computing device. And as shown at block 904, the operations may include controlling at least one functional element of the aerosol delivery device based on a state of the proximity-based communication link, or in response to a trigger signal received from the computing device over the proximity-based communication link.

In some examples, the functional element(s) of the aerosol delivery device may be controlled in an instance in which the proximity-based communication link is broken, and/or based on a signal strength of the proximity-based communication link.

In some examples, controlling at least one functional element of the aerosol delivery device may include controlling a sensory-feedback member to provide a user-perceptible feedback, and/or controlling at least one functional element to alter a locked state of the aerosol delivery device.

Figure 10:
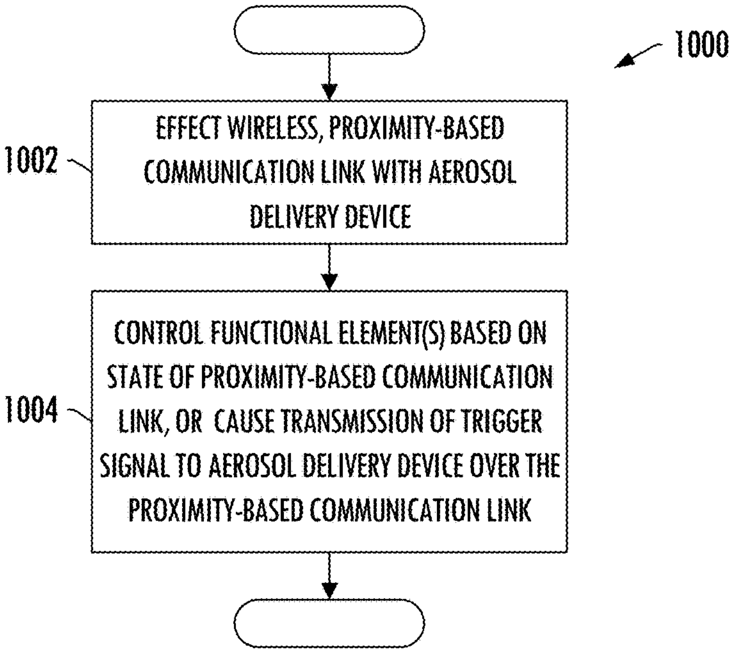
FIG. 10 illustrates various operations in a method of interacting with an aerosol delivery device, according to example implementations.

FIG. 10 illustrates various operations in a method 1000 of interacting with an aerosol delivery device including a heating element configured to activate and vaporize components of an aerosol precursor composition in response to a flow of air through at least a portion of the housing, with the air being combinable with a thereby formed vapor to form an aerosol. The method includes operations performed at a computing device. As shown at block 1002, these operations may include effecting a wireless, proximity-based communication link with the aerosol delivery device. And as shown at block 1004, the operations may include controlling at least one functional element of the computing device based on a state of the proximity-based communication link, or causing transmission of a trigger signal to the aerosol delivery device over the proximity-based communication link to effect control of the aerosol delivery device in response thereto.

In some examples, the method may include controlling the functional element(s) of the computing device. In these examples, the functional element(s) may be controlled in an instance in which the proximity-based communication link is broken, and/or based on a signal strength of the proximity-based communication link.

In some examples, the method may include causing transmission of the trigger signal. In these examples, causing transmission of the trigger signal may include causing transmission of the trigger signal to effect control of a sensory-feedback member of the aerosol delivery device to provide a user-perceptible feedback, and/or to alter a locked state of the aerosol delivery device.

It will be understood that each block of the flowcharts in FIGS. 9 and 10, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which may embody the procedures described herein may be stored by one or more memory devices of a computing device and executed by a processor in the computing device. In some examples, the computer program instructions comprising the computer program product(s) which embody the procedures described above may be stored by memory devices of a plurality of computing devices. As will be appreciated, any such computer program product may be implemented on a computer or other programmable apparatus to produce a machine, such that the computer program product including the instructions which execute on the computer or other programmable apparatus creates means for implementing the functions specified in the flowchart block(s).

Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s). Accordingly, blocks of the flowcharts support combinations of means for performing the specified functions. It will also be understood that one or more blocks of the flowcharts, and combinations of blocks in the flowcharts, may be implemented by special purpose hardware-based computer systems which perform the specified functions, or combinations of special purpose hardware and computer program product(s).

Moreover, it will be appreciated that the ordering of blocks and corresponding method operations within the flowchart is provided by way of non-limiting example in order to describe operations that may be performed in accordance some examples. In this regard, it will be appreciated that the ordering of blocks and corresponding method operations illustrated in the flowchart is non-limiting, such that the ordering of two or more block illustrated in and described with respect to the flowchart may be changed and/or method operations associated with two or more blocks may be at least partially performed in parallel in accordance with some examples. Further, in some examples, one or more blocks and corresponding method operations illustrated in and described with respect to the flowchart may be optional, and may be omitted.

The foregoing description of use of the article can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the articles illustrated in FIGS. 1-4 or as otherwise described above may be included in a computing device or aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:

a housing;

a heating element configured to activate and vaporize components of an aerosol precursor composition in response to a flow of air through at least a portion of the housing, the air being combinable with a thereby formed vapor to form an aerosol;

a communication interface configured to effect a wireless, proximity-based communication link with a computing device; and a microprocessor coupled to the communication interface and configured to control at least one functional element of the aerosol delivery device based on a state of the proximity-based communication link, including the microprocessor being configured to control a sensory-feedback member to provide a user-perceptible feedback based on the state of the proximity-based communication link.

2. The aerosol delivery device of claim 1, wherein the microprocessor is configured to control the sensory-feedback member to provide the user-perceptible feedback when the proximity-based communication link is broken.

3. The aerosol delivery device of claim 1, wherein the microprocessor is configured to control the sensory-feedback member to provide the user-perceptible feedback when a signal strength of the proximity-based communication link is below a threshold level.

4. The aerosol delivery device of claim 1, wherein the microprocessor is further configured to control at least one functional element to alter a locked state of the aerosol delivery device based on the state of the proximity-based communication link.

5. A computing device comprising:

a communication interface configured to effect a wireless, proximity-based communication link with an aerosol delivery device including:

a housing; and a heating element configured to activate and vaporize components of an aerosol precursor composition in response to a flow of air through at least a portion of the housing, the air being combinable with a thereby formed vapor to form an aerosol; and a processor coupled to the communication interface and configured to control at least one functional element of the computing device based on a state of the proximity-based communication link, including the processor being configured to control a sensory-feedback member to provide a user-perceptible feedback based on the state of the proximity-based communication link.

6. The computing device of claim 5, wherein the processor is configured to control the sensory-feedback member to provide the user-perceptible feedback when the proximity-based communication link is broken.

7. The computing device of claim 5, wherein the processor is configured to control the sensory-feedback member to provide the user-perceptible feedback when a signal strength of the proximity-based communication link is below a threshold level.

* * * * *